US011850311B2

(12) United States Patent
Yukuhiro et al.

(10) Patent No.: US 11,850,311 B2
(45) Date of Patent: Dec. 26, 2023

(54) ASENAPINE-CONTAINING ADHESIVE PATCH

(71) Applicant: Hisamitsu Pharmaceutical Co., Inc., Tosu (JP)

(72) Inventors: Masaki Yukuhiro, Tsukuba (JP); Yuka Takagi, Tsukuba (JP); Satoshi Amano, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 204 days.

(21) Appl. No.: 17/281,621

(22) PCT Filed: Sep. 25, 2019

(86) PCT No.: PCT/JP2019/037582
§ 371 (c)(1),
(2) Date: Mar. 31, 2021

(87) PCT Pub. No.: WO2020/071205
PCT Pub. Date: Apr. 9, 2020

(65) Prior Publication Data
US 2021/0369637 A1 Dec. 2, 2021

(30) Foreign Application Priority Data
Oct. 1, 2018 (JP) ................. 2018-186875

(51) Int. Cl.
*A61K 9/70* (2006.01)
*A61K 31/407* (2006.01)

(52) U.S. Cl.
CPC .......... *A61K 9/7069* (2013.01); *A61K 31/407* (2013.01)

(58) Field of Classification Search
CPC .. A61K 31/407; A61K 9/7069; A61K 9/7076; A61K 9/7038; A61K 47/20; A61K 47/10; A61K 47/12; A61K 47/183; A61K 47/22; A61P 25/18
See application file for complete search history.

(56) References Cited

U.S. PATENT DOCUMENTS

| | | |
|---|---|---|
| 2005/0019385 A1 | 1/2005 | Houze |
| 2006/0015077 A1 | 1/2006 | Cilurzo et al. |
| 2015/0164862 A1 | 6/2015 | Suzuki et al. |
| 2015/0202183 A1 | 7/2015 | Suzuki et al. |
| 2015/0231250 A1 | 8/2015 | Sonobe et al. |
| 2015/0290142 A1* | 10/2015 | Cawello ............... A61K 9/7084 604/307 |
| 2018/0193283 A1 | 7/2018 | Mohr et al. |
| 2018/0207108 A1 | 7/2018 | Sonobe et al. |
| 2019/0000775 A1 | 1/2019 | Yasukochi et al. |

FOREIGN PATENT DOCUMENTS

| | | |
|---|---|---|
| WO | WO 2010/127674 | 11/2010 |
| WO | WO 2014/017593 | 1/2014 |
| WO | WO 2014/017594 | 1/2014 |
| WO | WO 2014/017595 | 1/2014 |
| WO | WO 2017/018321 | 2/2017 |
| WO | WO 2017/018322 | 2/2017 |
| WO | WO 2017/131034 | 8/2017 |
| WO | WO 2018/115010 | 6/2018 |
| WO | WO 2019/002204 | 1/2019 |

OTHER PUBLICATIONS

PCT/JP2019/037582, dated Dec. 10, 2019, Translation of the International Search Report and Written Opinion.

* cited by examiner

*Primary Examiner* — Tracy Liu
*Assistant Examiner* — Lucy M Tien
(74) *Attorney, Agent, or Firm* — Wolf, Greenfield & Sacks, P.C.

(57) ABSTRACT

An object of the present invention is to provide an asenapine-containing patch having excellent adhesiveness and handleability, which can persistently provide sufficient medicinal effects by suppressing cold flow during storage or application while enhancing skin permeability using a silicone-based pressure-sensitive adhesive base, and thereby maintaining the stability of the drug in the patch during storage, and maintaining an appropriate administration form for a long period of time. The present invention relates to a patch having a support and a pressure-sensitive adhesive layer, wherein the pressure-sensitive adhesive layer comprises asenapine and a silicone-based pressure-sensitive adhesive base, and the loss tangent (tan δ) of the pressure-sensitive adhesive layer is 0.75 to 1.5 at 1.0 Hz.

12 Claims, No Drawings

ASENAPINE-CONTAINING ADHESIVE PATCH

RELATED APPLICATION

This application is a national stage filing under 35 U.S.C. § 371 of International Patent Application Serial No. PCT/JP2019/037582, filed Sep. 25, 2019, the content of which is incorporated by reference herein in its entirety.

TECHNICAL FIELD

The present invention relates to a patch containing asenapine in the pressure-sensitive adhesive layer and a method for producing the same.

BACKGROUND ART

Asenapine is known as a therapeutic agent for central nervous system diseases such as schizophrenia, and sublingual tablets (Sycrest® sublingual tablets and Saphris® sublingual tablets) are commercially available. At present, asenapine is not commercially available in dosage forms other than sublingual tablets.

Asenapine-containing patches are described in, for example, Patent documents 1 to 5, and all of them have been studied mainly for patches using rubber-based pressure-sensitive adhesive bases and acrylic-based pressure-sensitive adhesive bases.

An asenapine-containing patch in which a polysiloxane pressure-sensitive adhesive and a polyacrylate pressure-sensitive adhesive are combined is described in, for example, Patent document 6, in particular Example 14.

CITATION LIST

Patent Document

[Patent document 1] WO No. 2014/017593
[Patent document 2] WO No. 2014/017594
[Patent document 3] WO No. 2014/017595
[Patent document 4] WO No. 2017/018321
[Patent document 5] WO No. 2017/018322
[Patent document 6] WO No. 2010/127674

SUMMARY OF INVENTION

Problems to be Solved by the Invention

During examination of patches containing asenapine, present inventors have come to know that, regarding patches using asenapine and a silicone-based pressure-sensitive adhesive base, while they tend to have higher skin permeability than patches using a rubber-based pressure-sensitive adhesive base, cold flow (so-called "shita-dashi" in Japanese) is likely to occur in the pressure-sensitive adhesive base layer during storage or application, which affects the temporal stability of asenapine, leading to a decrease in the skin permeability with a decrease in asenapine content.

Cold flow is a phenomenon in which a pressure-sensitive adhesive flows/deforms at room temperature during storage or application. When cold flow occurs, the pressure-sensitive adhesive layer protrudes from the side surface of a patch on which a support and the pressure-sensitive adhesive layer are laminated, to the outside beyond the range covered by the support, and the shape of the patch cannot be maintained; and the following problems occur: for example, the protruding part of the pressure-sensitive adhesive layer adheres to the inner surface of the packaging material of the patch, which affects the temporal stability of asenapine, and the skin permeability decreases with a decrease in asenapine content, and it becomes difficult to remove the patch from the packaging material.

Therefore, an object of the present invention is to provide an asenapine-containing patch having excellent handleability, which can persistently provide sufficient medicinal effects by suppressing cold flow during storage or application while enhancing skin permeability using a silicone-based pressure-sensitive adhesive base, and thereby maintaining the stability of the drug in the patch and maintaining an appropriate administration form for a long period of time.

Means for Solving Problems

The present inventors have conducted extensive research to solve such a problem, and found that, by adjusting loss tangent (tan δ) of a pressure-sensitive adhesive layer within a predetermined range to suppress the cold flow of a patch containing asenapine and a silicone-based pressure-sensitive adhesive base, not only the patch has excellent adhesiveness and handleability, but also stability of the drug in the patch as well as an appropriate administration form for a long period of time can be maintained, and sufficient medicinal effects can be persistently obtained; as a result of further research, the present inventors have completed the present invention. That is, the present invention relates to the following.

[1] A patch comprising a support and a pressure-sensitive adhesive layer,
wherein the pressure-sensitive adhesive layer comprises asenapine and/or a pharmaceutically acceptable salt thereof, and a silicone-based pressure-sensitive adhesive base, and
wherein a loss tangent (tan δ) of the pressure-sensitive adhesive layer is 0.75 to 1.5 at 1.0 Hz.

[2] The patch according to [1], wherein the pressure-sensitive adhesive layer has a viscosity of 3,000 to 60,000 Pa·s at 90° C.

[3] The patch according to [1], wherein the pressure-sensitive adhesive layer has a viscosity of 3,500 to 60,000 Pa·s at 90° C.

[4] The patch according to any one of [1] to [3], wherein the silicone-based pressure-sensitive adhesive base comprises at least one selected from the group consisting of high-tack amine-compatible silicone-based pressure-sensitive adhesive bases, medium-tack amine-compatible silicone-based pressure-sensitive adhesive bases and low-tack amine-compatible silicone-based pressure-sensitive adhesive bases.

[5] The patch according to [4], wherein the silicone-based pressure-sensitive adhesive base comprises a high-tack amine-compatible silicone-based pressure-sensitive adhesive base and a medium-tack amine-compatible silicone-based pressure-sensitive adhesive base.

[6] The patch according to [5], wherein the mass ratio of the high-tack amine-compatible silicone-based pressure-sensitive adhesive base to the medium-tack amine-compatible silicone-based pressure-sensitive adhesive base is 90:10 to 10:90.

[7] The patch according to [4], wherein the silicone-based pressure-sensitive adhesive base comprises a high-tack amine-compatible silicone-based pressure-sensitive adhesive base and a low-tack amine-compatible silicone-based pressure-sensitive adhesive base.

[8] The patch according to [7], wherein the mass ratio of the high-tack amine-compatible silicone-based pressure-sensitive adhesive base to the low-tack amine-compatible silicone-based pressure-sensitive adhesive base is 90:10 to 30:70.

[9] The patch according to any one of [1] to [8], wherein the pressure-sensitive adhesive layer is composed of asenapine and a silicone-based pressure-sensitive adhesive base.

[10] The patch according to any one of [1] to [8], wherein the pressure-sensitive adhesive layer further comprises an antioxidant.

[11] The patch according to [10], wherein the pressure-sensitive adhesive layer is composed of asenapine, a silicone-based pressure-sensitive adhesive base, and an antioxidant.

[12] The patch according to [10] or [11], wherein the antioxidant is at least one selected from the group consisting of dibutylhydroxytoluene, mercaptobenzimidazole, ethylenediaminetetraacetic acid and citric acid.

[13] The patch according to any one of [1] to [12], wherein the mass of the pressure-sensitive adhesive layer is 30 to 200 g/m².

Advantageous Effects of Invention

According to the present invention, in a patch containing a silicone-based pressure-sensitive adhesive layer that comprises asenapine, cold flow can be suppressed and the form of the patch can be maintained, so that the patch is excellent in storage stability and handleability. Furthermore, the patch of the present invention is also excellent in adhesiveness.

EMBODIMENTS FOR CARRYING OUT INVENTION

The patch of the present invention comprises, for example, a support and a pressure-sensitive adhesive layer laminated on the support.

The support may be any one that can maintain the shape of the patch, in particular, of the pressure-sensitive adhesive layer. Examples of a material of the support include polyamides such as polyethylene, polypropylene, polybutadiene, ethylene-vinyl chloride copolymer, polyvinyl chloride, and nylon (trade name); synthetic resins such as polyester, cellulose derivatives, and polyurethane. The properties and condition of the support include, for example, films, sheets, sheet-like porous materials, sheet-like forms, fabrics such as woven fabrics, knitted fabrics, non-woven fabrics, and laminates thereof. The thickness of the support is not particularly limited, and is usually preferably about 2 to 3000 μm.

The pressure-sensitive adhesive layer comprises asenapine and a silicone-based pressure-sensitive adhesive base. In addition to asenapine and silicone-based pressure-sensitive adhesive bases, if necessary, the patches of the present invention may contain other additives such as antioxidants, tackifier resins, plasticizers, absorption promoters, solubilizers, cross-linking agents, antiseptics, fillers, preservatives, fragrances, etc.

The asenapine of the present invention is a compound also called trans-5-chloro-2-methyl-2,3,3a,12b-tetrahydro-1H-dibenz[2, 3:6,7]oxepino[4,5-c]pyrrole. Asenapine has a plurality of optical isomers, and any of the optical isomers can be used, and a mixture of optical isomers such as racemates may be used. The acid added to asenapine is not particularly limited as long as it is a pharmaceutically acceptable acid. The acid addition salt of asenapine may be anhydrous or hydrated.

Examples of the acid in the acid addition salt of asenapine include hydrochloric acid, hydrobromic acid, hydroiodic acid, phosphoric acid, acetic acid, propionic acid, glycolic acid, maleic acid, malonic acid, succinic acid, tartaric acid, citric acid, ascorbic acid, salicylic acid, benzoic acid, etc. For example, asenapine maleate is commercially available as sublingual tablets (Sycrest® sublingual tablets and Saphris® sublingual tablets).

The desalting agent may be any one as long as it can convert the acid addition salt of asenapine into an asenapine free base by a salt exchange reaction with the acid addition salt of asenapine. That is, the desalting agent means a component that converts an acid addition salt of asenapine into an asenapine free base. Examples of desalting agent include alkali metal hydroxides, alkali metal salts, alkaline earth metal hydroxides, alkaline earth metal salts, low molecular weight amines, etc., and one of these may be used alone, and two or more may be used in combination. Examples of alkali metal hydroxide include lithium hydroxide, sodium hydroxide, potassium hydroxide. Examples of alkali metal salt include sodium carbonate, potassium carbonate, sodium hydrogen carbonate, trisodium phosphate, disodium hydrogen phosphate, sodium dihydrogen phosphate, tripotassium phosphate, dipotassium hydrogen phosphate, potassium dihydrogen phosphate, sodium lactate, sodium citrate, disodium tartrate, sodium hydrogen tartrate, sodium oleate, etc. The low molecular weight amine is an amine having a molecular weight of 30 to 300, and examples thereof include monoethanolamine, diethanolamine, triethanolamine, isopropanolamine, and diisopropanolamine, etc. The desalting agent may be selected in consideration of pKa of the acid added to asenapine. When the desalting agent is sodium hydroxide or sodium acetate, the drug is less degraded during production of the patch.

The content of asenapine can be appropriately set by those skilled in the art, and it is preferably 0.5 to 30 mass % in terms of asenapine free form relative to the total amount of the pressure-sensitive adhesive layer, and it is more preferably 1 to 20 mass %, furthermore preferably 1.5 to 12 mass %, and particularly preferably 2 to 10 mass %.

In the patch of the present invention, the loss tangent (tan δ) of the pressure-sensitive adhesive layer at 1.0 Hz is preferably 0.75 to 1.5, preferably 0.85 to 1.5, more preferably 0.85 to 1.45, more preferably 0.85 to 1.3, and even more preferably 0.9 to 1.3. When the loss tangent is small, the adhesiveness tends to be poor and the production tends to be difficult, and when the loss tangent is large, cold flow tends to occur easily.

Loss tangent (tan δ), which is an index of viscoelasticity, is a value calculated by the formula below in a dynamic viscoelasticity measurement, wherein a composition containing asenapine and a silicone-based pressure-sensitive adhesive base is sandwiched between two plates, and a change in the stress when periodically vibrating strain is applied to one plate is measured. Here, the dynamic viscoelasticity measurement is performed, for example using a rotary rheometer at a temperature of 32° C. and a frequency of 1 Hz.

Loss tangent (tan δ)=Loss elastic modulus (G")/Storage elastic modulus (G')

The patch of the present invention has a viscosity at 90° C. of preferably 3,000 to 60,000 Pa·s, preferably 3,500 to 60,000 Pa·s, more preferably 4,500 to 55,000 Pa·s, more preferably 5,500 to 28,000 Pa·s, and even more preferably 5,500 to 20,000 Pa·s. When the viscosity at 90° C. is small, cold flow tends to occur easily, and when the viscosity at 90°

C. is large, the adhesiveness tends to be poor and the production tends to be difficult.

The viscosity in the present invention is a value obtained by measuring the viscosity of a sample (pressure-sensitive adhesive layer, etc.) at a predetermined temperature using a flow tester (Shimadzu Corporation, product name "FLOW-TESTER CFT-500"). The viscosity of the pressure-sensitive adhesive layer according to the present invention is a value measured by the above method for the pressure-sensitive adhesive layer upon its arrangement on the surface of the support.

The patch of the present invention has a cold flow area ratio of less than 40%, preferably less than 15%, and even more preferably less than 10%.

The cold flow area ratio in the present invention refers to a percentage of the area of a cold flow portion (the portion expanded from the original patch), when the area without cold flow (that is, the area of the original patch) is defined to be 100%.

The silicone-based pressure-sensitive adhesive base is a compound having an organopolysiloxane skeleton.

Examples of the silicone-based pressure-sensitive adhesive base include a mixture of silicone rubber and silicone resin, or a dehydration-condensation product thereof in the presence of an alkaline catalyst, etc.; and a condensation product of silicone rubber and silicone resin is preferable.

The silicone rubber constituting the silicone-based pressure-sensitive adhesive base is, for example, a long-chain polymer having hydroxy groups at both ends of polyorganosiloxane. As the organosiloxane unit of the silicone rubber, a silicone rubber containing dimethylsiloxane as a main component is preferable.

The silicone resin constituting the silicone-based pressure-sensitive adhesive base is not particularly limited, and a silicate resin having a three-dimensional structure is preferable.

Examples of the silicone-based pressure-sensitive adhesive base include dimethylpolysiloxane, polymethylvinylsiloxane, and polymethylphenylsiloxane. Specific silicone-based pressure-sensitive adhesive bases include, for example, MD series (Dow Corning Corp.) such as MD7-4502 Silicone Adhesive, MD7-4602 Silicone Adhesive; BIO-PSA series (Dow Corning Corp.) such as BIO-PSA® 7-4301 Silicone Adhesive, BIO-PSA® 7-4302 Silicone Adhesive, BIO-PSA® 7-4201 Silicone Adhesive, BIO-PSA® 7-4202 Silicone Adhesive, BIO-PSA® 7-4101 Silicone Adhesive, BIO-PSA® 7-4102 Silicone Adhesive, BIO-PSA® 7-4601 Silicone Adhesive, BIO-PSA® 7-4602 Silicone Adhesive, BIO-PSA® 7-4501 Silicone Adhesive, BIO-PSA® 7-4502 Silicone Adhesive, BIO-PSA® 7-4401 Silicone Adhesive, BIO-PSA® 7-4402 Silicone Adhesive, BIO-PSA® 7-4100 Silicone Adhesive, BIO-PSA® 7-4200 Silicone Adhesive, BIO-PSA® 7-4300 Silicone Adhesive, BIO-PSA® 7-4400 Silicone Adhesive, BIO-PSA® 7-4500 Silicone Adhesive, BIO-PSA® 7-4600 Silicone Adhesive; Dow Corning® 7-9800A, Dow Corning® 7-9800B, Dow Corning® 7-9700A, Dow Corning® 7-9700B.

The silicone-based pressure-sensitive adhesive base of the present invention is preferably an amine-compatible silicone-based pressure-sensitive adhesive base. The amine-compatible silicone-based pressure-sensitive adhesive base is a silicone-based pressure-sensitive adhesive base wherein, for example, after condensing polydimethylsiloxane and silicone resin, silanol groups that remain upon condensation by trimethylsilylation, etc. are blocked by trimethylsilyl groups, etc., thereby suppressing the remaining silanol concentration.

In addition, the silicone-based pressure-sensitive adhesive base can be roughly classified into three types: high tack, medium tack, and low tack, depending on the tack property; in the present invention, these can be appropriately combined and used.

According to JIS K6800-1985 or ISO6354, tack refers to the property of a pressure-sensitive adhesive that can form a bond immediately after contacting the surface of a material to be adhered with a very light force.

The high-tack amine-compatible silicone-based pressure-sensitive adhesive base in the present invention has a weight ratio of silicone resin to silicone rubber of approximately 52.5:47.5 (w/w) to 57.5:42.5 (w/w), and it is preferably an amine-compatible silicone-based pressure-sensitive adhesive base having 55:45 (w/w). Examples of high-tack amine-compatible silicone-based pressure-sensitive adhesive base include BIO-PSA® 7-4302 Silicone Adhesive and BIO-PSA® 7-4301 Silicone Adhesive.

The medium-tack amine-compatible silicone-based pressure-sensitive adhesive base in the present invention has a weight ratio of silicone resin to silicone rubber of approximately 57.5:42.5 (w/w) to 62.5:37.5 (w/w), and it is preferably an amine-compatible silicone-based pressure-sensitive adhesive base having 60:40 (w/w). Examples of the medium-tack amine-compatible silicone-based pressure-sensitive adhesive base include BIO-PSA® 7-4202 Silicone Adhesive and BIO-PSA® 7-4201 Silicone Adhesive.

The low-tack amine-compatible silicone-based pressure-sensitive adhesive base in the present invention has a weight ratio of silicone resin to silicone rubber of approximately 62.5:37.5 (w/w) to 67.5:32.5 (w/w), and it is preferably an amine-compatible silicone-based pressure-sensitive adhesive base having 65:35 (w/w). Examples of the low-tack amine-compatible silicone-based pressure-sensitive adhesive base include BIO-PSA® 7-4102 Silicone Adhesive and BIO-PSA® 7-4101 Silicone Adhesive.

In one embodiment, the present invention contains a high-tack amine-compatible silicone-based pressure-sensitive adhesive base and a medium-tack amine-compatible silicone-based pressure-sensitive adhesive base. The mass ratio of the high-tack amine-compatible silicone-based pressure-sensitive adhesive base to the medium-tack amine-compatible silicone-based pressure-sensitive adhesive base can be appropriately determined, and it is preferably 90:10 to 10:90, more preferably 87.5:12.5 to 12.5:87.5, and even more preferably 75:25 to 25:75.

In one embodiment, the present invention contains a high-tack amine-compatible silicone-based pressure-sensitive adhesive base and a low-tack amine-compatible silicone-based pressure-sensitive adhesive base. The mass ratio of the high-tack amine-compatible silicone-based pressure-sensitive adhesive base to the low-tack amine-compatible silicone-based pressure-sensitive adhesive base can be appropriately determined, and is preferably 90:10 to 30:70, more preferably 90:10 to 50:50, further preferably 87.5:12.5 to 50:50, and even more preferably 75:25 to 50:50.

Examples of antioxidants include tocopherols and their ester derivatives, ascorbic acid, ascorbyl stearate, nordihitolog ayaretic acid, dibutylhydroxytoluene (BHT), butylhydroxyanisole (BHA), citric acid, 2-mercaptobenzimidazole, and ethylenediamine tetraacetic acid. The antioxidant may be used alone or in combination of two or more.

The plasticizer may be any one that imparts flexibility to the pressure-sensitive adhesive layer. Examples of the plasticizer include mineral oils (e.g., paraffin oil, naphthenic oil, aromatic oils), animal oils (e.g., squalane, squalene), vegetable oils (e.g., olive oil, camellia oil, castor oil, tall oil, peanut oil), silicone oil, dibasic acid esters (e.g., dibutylphthalate, dioctylphthalate), liquid rubbers (e.g., liquid polybutene, liquid polyisoprene), liquid fatty acid esters (e.g., isopropylmyristate, hexyl laurate, diethyl sebacate, diisopropyl sebacate), polyhydric alcohols (e.g., diethylene glycol, polyethylene glycol, propylene glycol, dipropylene glycol), triacetin, triethyl citrate, crotamitone and the like. The plasticizer may be used alone or in combination of two or more.

The absorption promoter is a component that regulates the skin permeability of asenapine or its pharmaceutically acceptable salt. The absorption promoter is not particularly limited as long as it is a compound that has been conventionally recognized to have an absorption-promoting effect on the skin. Examples thereof include aliphatic alcohols such as isostearyl alcohol, fatty acids such as capric acid, fatty acid derivatives such as propylene glycol monolaurate, isopropyl myristate, isopropyl palmitate and diethanolamide laurate, and glycols such as propylene glycol and polyethylene glycol. The absorption promoter may be used alone or in combination of two or more.

The cross-linking agent is not particularly limited, and preferred examples include thermosetting resins such as amino resins, phenol resins, epoxy resins, alkyd resins, and unsaturated polyesters; isocyanate compounds, blocked isocyanate compounds, organic cross-linking agents, inorganic cross-linking agents such as metals and metal compounds, and the like.

The antiseptic is not particularly limited, and preferable examples include ethyl paraoxybenzoate, propyl paraoxybenzoate, butyl paraoxybenzoate and the like. The filler is not particularly limited, and preferred examples include calcium carbonate, magnesium carbonate, silicates (aluminum silicate, calcium silicate, magnesium silicate, etc.), and cellulose derivatives (hydroxypropyl cellulose, hydroxypropyl methyl cellulose, carboxymethyl cellulose, etc.).

Examples of the filler include aluminum hydroxide, calcium carbonate, magnesium carbonate, silicates (e.g., aluminum silicate, magnesium silicate), silicic acid, barium sulfate, calcium sulfate, calcium zincate, zinc oxide, titanium oxide, etc.

Examples of the preservative include disodium edetate, tetrasodium edetate, ethyl paraoxybenzoate, propyl paraoxybenzoate, butyl paraoxybenzoate, etc. The preservative may be used alone or in combination of two or more.

In one embodiment of the invention, the pressure-sensitive adhesive layer further comprises one or more selected from the group consisting of ascorbic acid, mercaptobenzimidazole and citric acid.

In one embodiment of the present invention, the mass of the pressure-sensitive adhesive layer is preferably 30 to 200 $g/m^2$, more preferably 30 to 150 $g/m^2$, and furthermore preferably 30 to 130 $g/m^2$. When the mass is too small, problems such as poor adhesiveness and difficulty in production may occur, and when the mass is too large, cold flow tends to occur easily and the physical properties may be deteriorated.

The patch may further comprise a release liner. The release liner is laminated on the pressure-sensitive adhesive layer on the surface opposite to the support side. When a release liner is provided, there is a tendency to reduce the adhesion of dust and the like to the pressure-sensitive adhesive layer during storage.

The material of the release liner is not particularly limited, and a film generally known to those skilled in the art can be used. Examples of the material of the release liner include polyesters such as polyethylene terephthalate and polyethylene naphthalate; polyolefins such as polyethylene and polypropylene; films such as polyvinyl chloride and polyvinylidene chloride; laminated films of high-quality paper and polyolefin; films such as Nylon® and aluminum, and the like. As the material of the release liner, polypropylene or polyethylene terephthalate is preferable.

Next, an example of the method for producing the patch of the present invention will be described.

First, a mixture for forming a pressure-sensitive adhesive layer is prepared. The mixture for forming a pressure-sensitive adhesive layer is obtained by dissolving or dispersing the above-mentioned asenapine, a silicone-based pressure-sensitive adhesive base, and other components in a solvent using a mixer.

As the solvent, toluene, hexane, ethyl acetate, cyclohexane, heptane, butyl acetate, ethanol, methanol, xylene, isopropanol, etc. can be used. These can be appropriately selected depending on the components to be dissolved or dispersed, and one type can be used alone or two or more types can be mixed and used in combination.

Next, the obtained mixture for forming the pressure-sensitive adhesive layer is spread directly on a support and dried to form the pressure-sensitive adhesive layer, and then a release liner for protecting the pressure-sensitive adhesive layer is adhered on the pressure-sensitive adhesive layer; alternatively, the obtained mixture for forming the pressure-sensitive adhesive layer is spread on a release-treated paper or film and dried to form a pressure-sensitive adhesive layer, then a support is placed on it to pressure-bond the pressure-sensitive adhesive layer onto the support; thus a patch is obtained.

EXAMPLES

Example 1. Preparation of Patch (High Tack+Medium Tack)

Patches 1 to 7 were prepared according to the composition shown in Table 1. The mass of the pressure-sensitive adhesive was 100 $g/m^2$ (set value).

TABLE 1

| Component | Patch | | | | | | |
|---|---|---|---|---|---|---|---|
| | 1 | 2 | 3 | 4 | 5 | 6 | 7 |
| Asenapine (free form) | 3.2 | 3.2 | 3.2 | 3.2 | 3.2 | 3.2 | 3.2 |
| Silicone PSA-4202 | 96.8 | 84.7 | 72.6 | 48.4 | 24.2 | 12.1 | 0 |
| Silicone PSA-4302 | 0 | 12.1 | 24.2 | 48.4 | 72.6 | 84.7 | 96.8 |
| Total | 100 | 100 | 100 | 100 | 100 | 100 | 100 |
| PSA-4202:PSA-4302 | 100:0 | 87.5:12.5 | 75:25 | 50:50 | 25:75 | 12.5:87.5 | 0:100 |

PSA-4202: BIO-PSA ® 7-4202 Silicone Adhesive (Dow Corning Corp.)
PSA-4302: BIO-PSA ® 7-4302 Silicone Adhesive (Dow Corning Corp.)

Example 2. Dynamic Viscoelasticity Test

Using patches 1, 3 to 7 as a sample, the loss elastic modulus and the storage elastic modulus were measured under the following conditions, and the loss tangent (tan δ value) was calculated (N=1 or 2).
[Measurement Conditions]
Equipment: HAAKE MARS III (Thermo Fisher Scientific Inc.)
Sample part: Parallel flat plates with 8-mm diameter
Gap spacing: 1 mm
Sample amount: 130 mg±10 mg
Temperature: 32° C.
Frequency: 1 Hz
Distortion: 1%

Table 2 shows the results of calculating the loss tangent (tan δ value) from the values of storage elastic modulus and loss elastic modulus obtained by the dynamic viscoelasticity test.

TABLE 2

| | Patch | | | | | |
|---|---|---|---|---|---|---|
| | 1 | 3 | 4 | 5 | 6 | 7 |
| tan δ value | 0.90 | 0.94 | 1.08 | 1.28 | 1.41 | 1.48 |

Example 3. Viscosity Measurement

The viscosities of patches 1, 3 to 7 at 90° C. were measured using a flow tester (Shimadzu Corporation, product name "FLOWTESTER CFT-500") under the following measurement conditions (N=2). The results are shown in Table 3.
[Measurement conditions]
Temperature rise: 5.0° C./min
Die hole diameter: 0.5 mm
Die length: 1.0 mm
Test weight: 50.0 kg

TABLE 3

| | Patch | | | | | |
|---|---|---|---|---|---|---|
| | 1 | 3 | 4 | 5 | 6 | 7 |
| Viscosity (Pa·s) | 52215 | 19735 | 10274 | 5730.5 | 4289.5 | 3161.0 |

Example 4. Cold Flow Evaluation Test

After applying a weight of 1 kg on patches 3 to 6 (circular, 2.49 cm$^2$) (cold flow induction), the patches were stored in a thermo-hygrostat at 32° C. and 60% RH for 48 hours, and the cold flow area ratio (percentage of the area of the cold flow portion relative to the area with no cold flow (circular, 2.49 cm$^2$)) was calculated (N=3). The results are shown in Table 4.

TABLE 4

| | Patch | | | |
|---|---|---|---|---|
| | 3 | 4 | 5 | 6 |
| Cold flow area ratio (%) | 2.95 | 6.04 | 7.86 | 13.63 |

The cold flow area ratios of the patches 3 to 6 were all less than 15% and good results were obtained. In addition, the cold flow area ratios of the patches 3 to 5 were all less than 10%, and even better results were obtained.

Example 5. Temporal Stability Test

Patches 8 to 17 were prepared according to the composition shown in Table 5.

TABLE 5

| | Patch | | | | | | | | | |
|---|---|---|---|---|---|---|---|---|---|---|
| | 8 | 9 | 10 | 11 | 12 | 13 | 14 | 15 | 16 | 17 |
| Asenapine maleate | 6 | 6 | 6 | 6 | 6 | 6 | 6 | 6 | 6 | 6 |
| Silicone PSA-4202 | 89.1 | 88.1 | 88.1 | 88.1 | 88.1 | 88.1 | 88.1 | 88.1 | 88.1 | 88.1 |
| Dibutylhydroxytoluene | — | 1 | — | — | — | — | — | — | — | — |
| Butylhydroxyanisole | — | — | 1 | — | — | — | — | — | — | — |
| Ascorbic acid | — | — | — | 1 | — | — | — | — | — | — |
| Tocopherol | — | — | — | — | 1 | — | — | — | — | — |
| Sodium pyrosulphite | — | — | — | — | — | 1 | — | — | — | — |
| Mercaptobenzimidazole | — | — | — | — | — | — | 1 | — | — | — |
| Ethylenediamine tetraacetic acid | — | — | — | — | — | — | — | 1 | — | — |
| 1,3-Butylene glycol | — | — | — | — | — | — | — | — | 1 | — |
| Citric acid | — | — | — | — | — | — | — | — | — | 1 |
| Other components | 4.9 | 4.9 | 4.9 | 4.9 | 4.9 | 4.9 | 4.9 | 4.9 | 4.9 | 4.9 |
| Total | 100 | 100 | 100 | 100 | 100 | 100 | 100 | 100 | 100 | 100 |

Patches 8 to 17 are individually packaged in an aluminum bag, and asenapine analogs were measured at immediately after production and after storage at 60° C. for 2 weeks (60° C.2W), under the following measurement conditions using high performance liquid chromatography (HPLC). The results are shown in Table 6.

[Measurement conditions]
Column: ODS column
Mobile phase solution: Methanol/(0.01 mol/L sodium lauryl sulfate in 0.1% phosphate solution)=3/1
Detection wavelength: 230 nm The numbers in parentheses in the table indicate the relative retention time RRT of an arbitrary analog, which is calculated as follows.

[Relative retention time of arbitrary analog (RRT)]=
[Retention time of peak of arbitrary analog (RT)]÷[Retention time of peak of asenapine (RT)]

In addition, the amount of analog (%) is calculated as follows.

[Amount of analog (%)]=[Peak area of arbitrary analog]÷[Peak area of asenapine]×100

TABLE 6

|  | Analog A, RRT(0.59) | | Analog B, RRT(1.13) | | Analog C, RRT(2.07) | |
| --- | --- | --- | --- | --- | --- | --- |
| Patch | Just after production | 60° C. 2 W | Just after production | 60° C. 2 W | Just after production | 60° C. 2 W |
| 8 | 0.188 | 0.084 | 0.000 | 0.557 | 0.000 | 0.053 |
| 9 | 0.135 | 0.000 | 0.000 | 0.158 | 0.000 | 0.000 |
| 10 | 16.142 | 15.958 | 0.146 | 1.712 | 0.041 | 0.086 |
| 11 | 0.238 | 0.176 | 1.684 | 2.858 | 0.000 | 0.000 |
| 12 | 0.000 | 0.000 | 0.000 | 1.392 | 0.067 | 0.000 |
| 13 | 0.000 | 0.000 | 1.101 | 0.000 | 0.000 | 0.000 |
| 14 | 0.000 | 0.000 | 0.000 | 0.000 | 0.000 | 0.054 |
| 15 | 0.000 | 0.000 | 0.193 | 0.307 | 0.000 | 0.000 |
| 16 | 0.000 | 0.000 | 0.291 | 1.403 | 0.000 | 0.000 |
| 17 | 0.000 | 0.000 | 0.040 | 0.476 | 0.000 | 0.000 |

Patch 9 (containing dibutylhydroxytoluene), patch 14 (containing mercaptobenzimidazole), patch 15 (containing ethylenediaminetetraacetic acid) and patch 17 (containing citric acid) have relatively low asenapine analogs compared to patch 8, indicating that asenapine was more stable.

Example 6. Preparation of Patch (High Tack+Low Tack)

Patches 18 to 25 were prepared according to the composition shown in Table 7. The mass of the pressure-sensitive adhesive was 100 g/m² (set value).

TABLE 7

| | Patch | | | | | | | |
| --- | --- | --- | --- | --- | --- | --- | --- | --- |
| Component | 18 | 19 | 20 | 21 | 22 | 23 | 24 | 25 |
| Asenapine (free form) | 3.2 | 3.2 | 3.2 | 3.2 | 3.2 | 3.2 | 3.2 | 3.2 |
| Silicone PSA-4102 | 96.8 | 84.7 | 72.6 | 48.4 | 24.2 | 12.1 | 0 | 0 |
| Silicone PSA-4302 | 0 | 12.1 | 24.2 | 48.4 | 72.6 | 84.7 | 96.8 | 91.8 |
| Silicone oil (dimethicone 20 cSt) | 0 | 0 | 0 | 0 | 0 | 0 | 0 | 5 |
| Total | 100 | 100 | 100 | 100 | 100 | 100 | 100 | 100 |
| PSA-4102:PSA-4302 | 100:0 | 87.5:12.5 | 75:25 | 50:50 | 25:75 | 12.5:87.5 | 0:100 | 0:100 |
| Loss tangent (tan δ) | 0.50 | 0.59 | 0.68 | 0.90 | 1.26 | 1.50 | 1.48 | 1.78 |
| Viscosity (Pa·s) | — | — | — | 26820 | 10072 | 5688 | 3161 | — |
| Cold flow area ratio (%) | 2.79 | 1.06 | 1.64 | 2.80 | 4.82 | 10.08 | 36.50 | 74.00 |
| Content relative to initial content (%) 60° C. 2 W | 96.81 | 91.11 | 82.68 | 82.91 | 84.1 | 81.77 | 80.5 | 75.54 |
| Probe tack value (gf) | — | 116 | 201 | 333 | 515 | 528 | — | — |

PSA-4102: BIO-PSA ® 7-4102 Silicone Adhesive (Dow Corning Corp.)
PSA-4302: BIO-PSA ® 7-4302 Silicone Adhesive (Dow Corning Corp.)
Silicone oil (dimethicone 20 cSt): Q7-9120 Silicone Fluid ® 20 cSt (Dow Corning Corp.)

In the table, the loss tangent (tan δ), viscosity (Pa·s) and cold flow area ratio (%) were measured or calculated using the methods described in Examples 2 to 4.

In the table, the content of asenapine relative to the initial content (content relative to initial content (%)) was calculated as follows.

<Calculation of the Content Relative to Initial Content (%)>

The prepared patches are individually packaged in an aluminum bag, and asenapine contents were measured at immediately after production and after storage at 60° C. for 2 weeks (60° C.2W), under the following measurement conditions using high performance liquid chromatography (HPLC).

[Measurement Conditions]
Column: ODS column
Mobile phase solution: Methanol/(0.01 mol/L sodium lauryl sulfate in 0.1% phosphate solution)=3/1
Detection wavelength: 230 nm The content relative to initial content is calculated as follows.

[Content relative to initial content (%)]=[Asenapine content after storage at 60° C.2W]÷[Asenapine content immediately after production]×100

In the table, the probe tack value (gf) was measured as follows.

<Measurement of Probe Tack Value (Gf)>

Measurement was performed using a probe tack tester (Rigaku Kogyo Co., Ltd., product name "Probe tack tester with digital counter"). The probe tack test conditions are as follows.

[Probe tack test conditions]
Probe material: Stainless steel
Probe diameter: 5 mmφ
Contact time: 1 sec
Contact weight: 4.9 N/cm$^2$
Peeling speed: 10 mm/sec As shown in Table 7, it was confirmed that patches 18 to 20 had a low cold flow area ratio and cold flow of the pressure-sensitive adhesive layer was suppressed; however, the adhesiveness was low. In addition, it was confirmed that the patch 25 had a large cold flow area ratio, and cold flow of the pressure-sensitive adhesive layer could not be suppressed. In contrast, it was confirmed that in patches 21 to 24, cold flow of the pressure-sensitive adhesive layer was suppressed and the patches had more excellent adhesiveness.

Example 7. Examination of Drug Concentration

Patches 26 to 28 were prepared according to the composition shown in Table 8. The mass of the pressure-sensitive adhesive was 100 g/m$^2$ (set value).

TABLE 8

| | Patch | | |
|---|---|---|---|
| Component | 26 | 27 | 28 |
| Asenapine (free form) | 2 | 7 | 10 |
| Silicone PSA-4202 | 98 | 93 | 90 |
| Total (%) | 100 | 100 | 100 |
| Loss tangent (tan δ) | 0.85 | 0.94 | 0.97 |
| Viscosity (Pa · s) | — | 27665 | 16985 |
| Cold flow area ratio (%) | 1.06 | 1.64 | 2.80 |

In the table, the loss tangent (tan δ), viscosity (Pa·s) and cold flow area ratio (%) were measured or calculated using the methods described in Examples 2 to 4.

As shown in Table 8, it was confirmed that even when the drug concentration was changed, the cold flow area ratio was lowered by setting the loss tangent (tan δ) within the predetermined range.

Example 8. Examination of the Mass of Pressure-Sensitive Adhesive

Patches 29 to 32 were prepared according to the composition shown in Table 9.

TABLE 9

| | Patch | | | |
|---|---|---|---|---|
| Component | 29 | 30 | 31 | 32 |
| Asenapine (free form) | 3.2 | 3.2 | 3.2 | 3.2 |
| Silicone PSA-4202 | 96.8 | 96.8 | 96.8 | 96.8 |
| Total (%) | 100 | 100 | 100 | 100 |
| Mass of adhesive (g/m$^2$) | 30 | 130 | 150 | 200 |
| Loss tangent (tan δ) | 0.90 | 0.90 | 0.90 | 0.90 |
| Cold flow area ratio (%) | 0.29 | 2.59 | 2.66 | 3.34 |

In the table, the loss tangent (tan δ) and the cold flow area ratio (%) were measured or calculated using the methods described in Examples 2 and 4.

As shown in Table 9, it was confirmed that even when the mass of the pressure-sensitive adhesive was changed within the range of 30 to 200 g/m$^2$, the cold flow area ratio was lowered by setting the loss tangent (tan δ) within the predetermined range.

The invention claimed is:

1. A patch comprising:
    (A) a support layer; and
    (B) a pressure-sensitive adhesive layer comprising:
        (i) asenapine and/or a pharmaceutically acceptable salt thereof, and
        (ii) a silicone-based pressure-sensitive adhesive base comprising:
            (a) at least one high-tack amine-compatible silicone-based pressure-sensitive adhesive base having a weight ratio of silicone resin to silicone rubber of approximately 52.5:47.5 (w/w) to 57.5:42.5 (w/w) and at least one low-tack amine-compatible silicone-based pressure-sensitive adhesive base having a weight ratio of silicone resin to silicone rubber of approximately 62.5:37.5 (w/w) to 67.5:32.5 (w/w); or
            (b) at least one medium-tack amine-compatible silicone-based pressure-sensitive adhesive base having a weight ratio of silicone resin to silicone rubber of approximately 57.5:42.5 (w/w) to 62.5:37.5 (w/w) and at least one low-tack amine-compatible silicone-based pressure-sensitive adhesive base having a weight ratio of silicone resin to silicone rubber of approximately 62.5:37.5 (w/w) to 67.5:32.5 (w/w), wherein a loss tangent (tan δ) of the pressure-sensitive adhesive layer is 0.85 to 1.3 at 1.0 Hz, and the pressure-sensitive adhesive layer has a viscosity of 5,500 to 28,000 Pa·s at 90° C.

2. The patch according to claim 1, wherein the silicone-based pressure-sensitive adhesive base comprises at least one high-tack amine-compatible silicone-based pressure-sensitive adhesive base and at least one low-tack amine-compatible silicone-based pressure-sensitive adhesive base.

3. The patch according to claim 2, wherein the mass ratio of the at least one high-tack amine-compatible silicone-based pressure-sensitive adhesive base to the at least one low-tack amine-compatible silicone-based pressure-sensitive adhesive base is 75:25 to 50:50.

4. The patch according to claim 1, wherein the pressure-sensitive adhesive layer is composed of asenapine and the silicone-based pressure-sensitive adhesive base.

5. The patch according to claim 1, wherein the pressure-sensitive adhesive layer further comprises an antioxidant.

6. The patch according to claim 5, wherein the pressure-sensitive adhesive layer is composed of asenapine, the silicone-based pressure-sensitive adhesive base, and an antioxidant.

7. The patch according to claim 5, wherein the antioxidant is at least one selected from the group consisting of dibutylhydroxytoluene, mercaptobenzimidazole, ethylenediaminetetraacetic acid and citric acid.

8. The patch according to claim 1, wherein the mass of the pressure-sensitive adhesive layer is 30 to 200 g/m$^2$.

9. The patch according to claim 1, wherein the silicone-based pressure-sensitive adhesive base comprises at least one medium-tack amine-compatible silicone-based pressure-sensitive adhesive base and at least one low-tack amine-compatible silicone-based pressure-sensitive adhesive base.

10. A patch comprising:
(A) a support layer; and
(B) a pressure-sensitive adhesive layer consisting of:
(i) asenapine and/or a pharmaceutically acceptable salt thereof, and
(ii) a silicone-based pressure-sensitive adhesive base consisting of at least one high-tack amine-compatible silicone-based pressure-sensitive adhesive base having a weight ratio of silicone resin to silicone rubber of approximately 52.5:47.5 (w/w) to 57.5:42.5 (w/w) and at least one medium-tack amine-compatible silicone-based pressure-sensitive adhesive base having a weight ratio of silicone resin to silicone rubber of approximately 57.5:42.5 (w/w) to 62.5:37.5 (w/w), and
(iii) optionally, an antioxidant, a tackifier resin, a plasticizer, an absorption promoter, a cross-linking agent, an antiseptic, a filler, a preservative, and/or a fragrance, wherein a loss tangent (tan δ) of the pressure-sensitive adhesive layer is 0.85 to 1.3 at 1.0 Hz, and
the pressure-sensitive adhesive layer has a viscosity of 5,500 to 28,000 Pa·s at 90° C.

11. The patch according to claim 10, wherein the mass ratio of the high-tack amine-compatible silicone-based pressure-sensitive adhesive base to the medium-tack amine-compatible silicone-based pressure-sensitive adhesive base is 75:25 to 25:75.

12. The patch according to claim 10, wherein the mass of the pressure-sensitive adhesive layer is 30 to 200 g/m$^2$.

* * * * *